United States Patent [19]

Rabin et al.

[11] Patent Number: 5,167,237
[45] Date of Patent: Dec. 1, 1992

[54] APPARATUS FOR MONITORING DETRUSOR PRESSURE EXERTED BY A BLADDER

[75] Inventors: Jill M. Rabin, New York; Gopal H. Badlani, Laurel Hollow, both of N.Y.

[73] Assignee: Long Island Jewish Medical Center, New Hyde Park, N.Y.

[21] Appl. No.: 727,554

[22] Filed: Jul. 9, 1991

[51] Int. Cl.[5] .............................................. A61B 5/00
[52] U.S. Cl. .................................... 128/748; 128/778; 128/774; 128/836
[58] Field of Search ............... 128/748, 774, 778, 834, 128/836, DIG. 25, 630, 761, 788; 600/29, 30

[56] References Cited

U.S. PATENT DOCUMENTS

| | | | |
|---|---|---|---|
| 3,866,613 | 2/1975 | Kenny et al. | 128/834 |
| 4,106,511 | 8/1978 | Erlandsson | 128/788 |
| 4,216,783 | 8/1980 | Kaiser et al. | 128/778 |
| 4,484,585 | 11/1984 | Baier | 128/748 |
| 4,612,939 | 9/1986 | Robertson | 128/774 |
| 4,757,194 | 7/1988 | Simms | 250/227.21 |
| 4,790,328 | 12/1988 | Young | 128/748 |
| 4,823,814 | 4/1989 | Drogendijk et al. | 128/834 |
| 4,825,875 | 5/1989 | Ninan et al. | 128/748 |
| 4,850,358 | 7/1989 | Millar | 128/637 |
| 4,873,990 | 10/1989 | Holmes et al. | 128/748 |
| 4,881,526 | 11/1989 | Johnson et al. | 128/788 |
| 4,909,263 | 3/1990 | Norris | 128/788 |
| 4,946,449 | 8/1990 | Davis, Jr. | 604/256 |
| 5,041,092 | 8/1991 | Barwick | 604/104 |
| 5,065,772 | 11/1991 | Cox, Jr. | 128/836 |

OTHER PUBLICATIONS

James et al., "The Vagina as an Alternative...", British Journal of Urology, vol. 60, pp.212-216, 1987.

Primary Examiner—Max Hindenburg
Assistant Examiner—Guy V. Tucker
Attorney, Agent, or Firm—Amster, Rothstein & Ebenstein

[57] ABSTRACT

A vesicovaginal apparatus for ambulatory monitoring of the detrusor pressure exerted by a bladder includes a first transducer configured and dimensioned for insertion into and retention by the bladder of a wearer during ambulatory motion for sensing the total pressure within the bladder, and a second transducer configured and dimensioned for insertion into and retention by the vagina of a wearer during ambulatory motion for sensing the pressure within the vagina. A portable recorder in operative communication with the first and second transducers records the total pressure sensed in the bladder and the pressure sensed in the vagina, with the difference indicating the detrusor pressure exerted by the bladder of the wearer.

6 Claims, 2 Drawing Sheets

APPARATUS FOR MONITORING DETRUSOR PRESSURE EXERTED BY A BLADDER

BACKGROUND OF THE INVENTION

The present invention relates to apparatus for the ambulatory monitoring of the detrusor pressure exerted by a bladder, and more particularly to a vesicovaginal apparatus therefor.

Conventional urodynamic assessment, performed most often in the urodynamic laboratory during a brief recording time and under nonphysiologic circumstances, may fail to reveal the exact nature of existing pathologic conditions of the lower urinary tract. One of the most clinically challenging groups of patients are those who present sensory urgency as their sole symptom. Sensory urgency is defined by the International Continence Society as "urgency and frequency as apparently isolated symptoms in the absence of demonstrable detrusor contractions." In order to make the diagnosis of sensory urgency, all of the other conditions which may cause abnormal contractility of the detrusor muscle must be ruled out. These include urinary tract infection, bladder or urethral calculi, bladder tumor, neuropathic lesions, pharmacologic manipulations and intrinsic muscle dysfunction.

Urodynamic studies are utilized as a foundation to understand the pathophysiology of the lower urinary tract, and, when combined with the history and physical examination, permit accurate diagnosis and formulation of a logical treatment plan. In patients experiencing sensory urgency as their only symptom, and in whom all other pathophysiology has been ruled out, this logical progression from diagnosis to treatment is frequently interrupted as the recorded tests often fail to correlate with the patient's symptoms. These studies may fail to show detrusor reflex contractions during routine cystometry, despite various detrusor provocative maneuvers, such as coughing, alteration in position or valsalva. Continuous bladder monitoring has proven to truly be a breakthrough in the diagnosis and treatment of these patients Ambulatory monitoring studies performed thus far have revealed occult bladder instability in a substantial proportion of these patients.

Various attempts have been made to monitor changes in bladder pressure on a continuous basis, utilizing liquid or air-coupled systems as well as telemetric techniques. Solid-state microtip transducers presently offer the best reproducibility with which to obtain reliable pressure signals during ambulatory monitoring. Preliminary studies indicate that the results of continuous monitoring utilizing natural fill cystometry are consistent with the clinical history of sensory urgency and urge incontinence, whereas conventional provocative cystometric techniques may give false or negative results.

To date, ambulatory monitoring has employed an intravesical pressure or bladder situated transducer in order to measure bladder pressures directly and either a transrectal or transurethral pressure transducer as an indirect measure of intraabdominal pressure. Subtracted pressure then yields true detrusor or intrinsic bladder pressure. However, since a twenty-four transrectal monitor is used as a reflection of intraabdominal pressure measurements, fecal impaction and rectal motility can often affect the results. The transrectal monitor is uncomfortable and therefore results in low patient compliance with the instructions of the doctor. Additionally, the transrectal monitor must be removed for each defecation or passage of flatus, thereby interfering with the study and further lowering patient compliance since handling of the transrectal monitor is understandably distasteful to most patients. Thus the disadvantages of a transrectal monitor in terms of patient comfort, patient compliance, and accuracy are well known in the art and need not be set forth herein in any detail.

Intraabdominal pressure has also been measured by using a transducer situated in the proximal one third of the urethra. However, although the proximal one-third of the urethra is of intraabdominal origin and therefore reflects this pressure, smooth and striated muscle, as well as vascular, elastic and connective tissue, each exert their own influence in contributing to intrinsic urethral pressure. Accordingly, transurethral pressure measurements may not simply reflect intraabdominal pressure and are considered separate essential parameters of a complete urological workup.

In the laboratory setting, intravaginal pressure measurements have been demonstrated to reflect intraabdominal pressure more accurately and consistently than transrectal or transurethral pressure measurements, provided the sensor is positioned in the upper two-thirds of the vagina, above the urogenital diaphragm. The vagina is less subject to physiological processes than the rectum; for example, it is less subject to variation secondary to fecal impaction and rectal motility, is less subject to artificially-induced contractions, and in general undergoes less movement (at least in its upper two-thirds). A transvaginal monitor is thus not only more accurate, but results in generally higher levels of patient compliance since it need not be removed to effect evacuation and is reported to be quite comfortable to the wearer. Thus far, urodynamic studies using the vagina as an alternative to the rectum in measuring intraabdominal pressure have been performed during conventional laboratory cystometric testing, where the transvaginal transducer was taped to the patient's inner thigh and connected by trailing wires to the urodynamic equipment. James, E. D., et al., "The Vagina as an Alternative to the Rectum in Measuring Abdominal Pressure During Urodynamic Investigations," *Br.J. Urol.* 60:212–16 (1987). The intravaginal catheter was held in place securely 8 cm from the introitus by a balloon inflated to 5 cc and taped to the patient's inner thigh. This has allowed catheter stability, but has not allowed patient ambulation. To date, there are no fully ambulatory studies of this kind.

Thus, the need remains to investigate the clinical, diagnostic and therapeutic capabilities of ambulatory bladder monitoring in women utilizing a transvaginal monitor as a reflection of intraabdominal pressure. Total bladder pressure will be measured directly, and true bladder pressure (detrusor pressure) will be determined by subtraction (bladder pressure minus transvaginally-determined intraabdominal pressure).

Accordingly, it is an object of the present invention to provide vesicovaginal apparatus for ambulatory monitoring of the detrusor pressure exerted by a bladder.

Another object is to provide such apparatus which avoids the disadvantages associated with transrectal or transurethral pressure determinations in terms of comfort, accuracy and patient compliance and secondary variations such as fecal impaction and rectal motility.

Another object is to provide such apparatus which is not affected by rectal motility and fecal impaction.

It is also an object of the present invention to provide such apparatus which is of simple and economical construction, and easy to maintain and use.

SUMMARY OF THE INVENTION

It has now been found that the above and related objects of the present invention are obtained in a vesicovaginal apparatus for ambulatory monitoring of the detrusor pressure exerted by a bladder. Basically the vesicovaginal apparatus comprises first transducer means configured and dimensioned for insertion into and retention by the bladder of a wearer during ambulatory motion for sensing the total pressure within the bladder, and second transducer means configured and dimensioned for insertion into and retention by the vagina of a wearer during ambulatory motion for sensing the pressure within the vagina. Portable means are in operative communication with the first and second transducer means for recording the total pressure sensed in the bladder and the pressure sensed in the vagina, with the difference indicating the detrusor pressure exerted by the bladder of the wearer.

In a preferred embodiment, the second transducer means is configured and dimensioned for insertion into and retention by the upper two-thirds of the vagina and comprises a transducer for sensing pressure and a pessary, preferably an precludes unintended separation of the transducer therefrom but, when deflated, enables easy separation of the transducer therefrom.

Preferably each of the first and second transducer means includes a microtip transducer for sensing pressure, the microtip transducers of the first and second transducer means being disposed in the bladder and the vagina, respectively, while the portable means is disposed externally of the body of the wearer.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
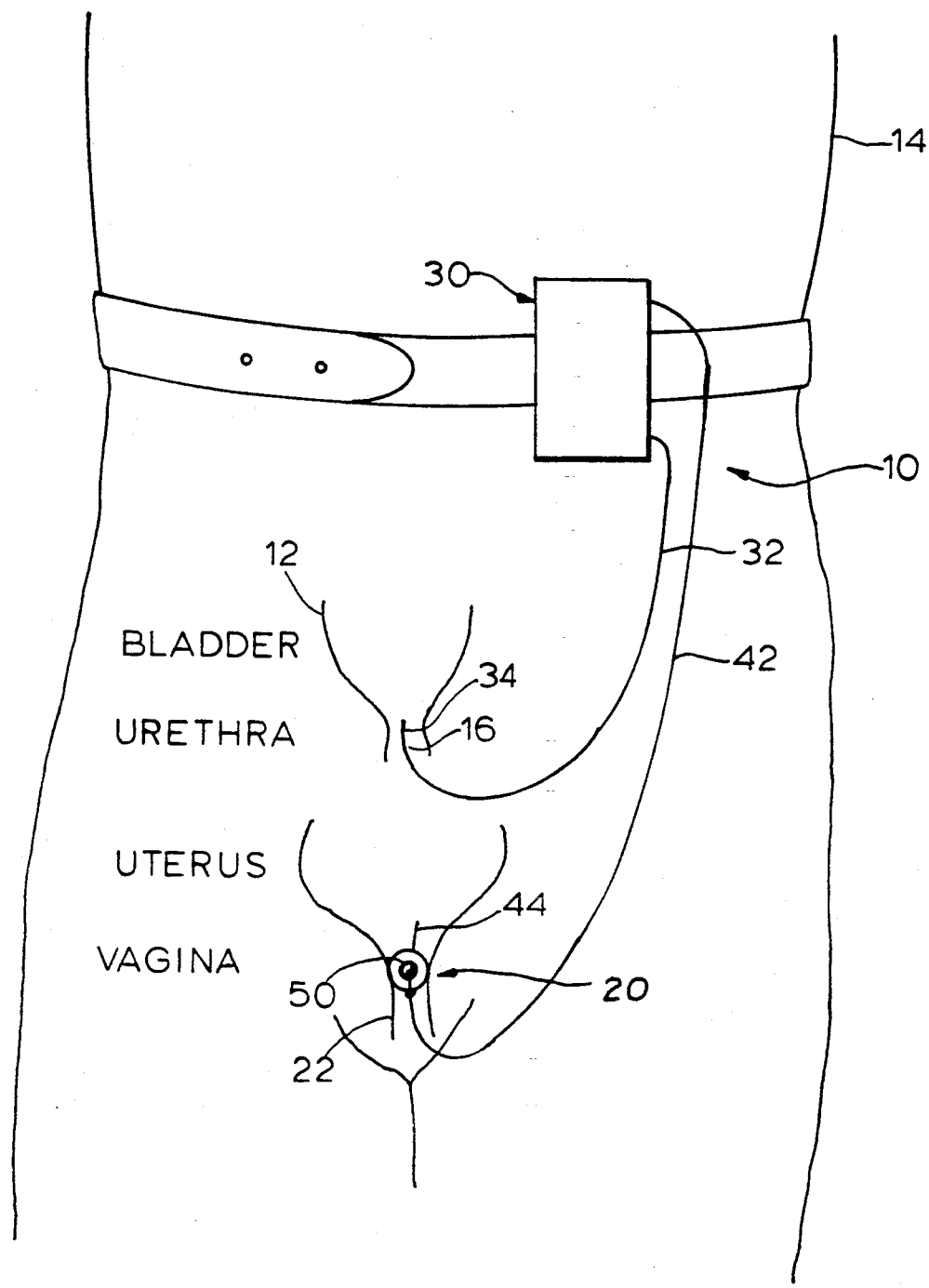
FIG. 1 is a schematic fragmentary front elevational view of a female wearing apparatus according to the present invention.

Referring now to the drawing, and in particular to FIG. 1 thereof, therein illustrated schematically is a female wearing vesicovaginal apparatus according to the present invention, generally designated by the reference numeral 10. The apparatus permits ambulatory monitoring of the detrusor pressure exerted by the bladder 12 of the female wearer 14. It will be appreciated that, for expository purposes, in FIG. 1 the relative locations of the pertinent anatomical portions of the wearer 14 have been relocated to afford a clearer view of each as it pertains to the present invention.

More particularly, the apparatus 10 comprises first transducer means, generally designated 16, configured and dimensioned for insertion into and retention by the bladder 12 of the wearer 14 during ambulatory motion of the wearer 14. The first transducer means 16 senses the total pressure within the bladder, this total pressure being a composite of the detrusor pressure exerted by the detrusor muscle of the bladder and the intraabdominal pressure. The apparatus 10 additionally comprises second transducer means, generally designated 20, configured and dimensioned for insertion into and retention by the vagina 22 of the wearer, preferably in the upper two thirds of the vagina 22. Finally, the apparatus 10 includes portable means, generally designated 30, in operative communication with the first and the second transducer means 16, 20 for recording the pressure sensed in the bladder by the first transducer means 16 and the pressure sensed in the vagina by the second transducer means 20. The portable means 30 may also determine (by subtraction) and record the difference between the pressure sensed in the bladder and the pressure sensed in the vagina as an indication of the detrusor pressure exerted by the bladder 12 of the wearer 14. The portable means 30 records each of these quantities so that they may be subsequently examined and compared over time, especially for comparison with the patient's symptomatic complaints.

It will be appreciated that the first or bladder transducer means 16 and the portable means 30 may be similar in structure and function to comparable apparatus used in conventional urodynamic studies. For example, transducer means 16 is preferably a catheter-mounted pressure-sensitive microtip transducer. The catheter 32 is a semi-flexible, dacron or silicone, size 4F Millar catheter, with the pressure-sensitive microtransducer 34 mounted at the tip. The catheter 32 and transducer 34 will be appropriately sterilized, and the transducer 34 also calibrated, before insertion under strict aseptic conditions. As the average transurethral diameter is slightly larger than 14F in the female, the patient will be able to void easily around the intravesical catheter 32. While this is a preferred first transducer means 16 for use in the present invention, it will be appreciated by those skilled in the art that a variety of other transducer means may be employed to achieve the same function. As such transducer means are well known in the art, a further description thereof is not deemed necessary herein.

The portable means 30 in operative communication with the first and second transducer means 16, 20 will record, on the one hand, both the pressure sensed in the bladder and the pressure sensed in the vagina, or, on the other hand, only the difference therebetween. If desired, the portable means may also record both—that is, the pressure sensed in the bladder, the pressure sensed in the vagina, and the difference therebetween, as an indication of the detrusor pressure exerted by the bladder of the wearer.

Depending upon the form of the output of the particular transducers 16, 20 and the acceptable form of input for the portable means 30 employed, the connecting catheters may utilize liquid (hydraulic media), gas (pneumatic media) or electricity as the coupling medium. A gas such as air is preferably used as the coupling medium to reduce the artifact with rapid movement of patient or catheter which is present in liquid coupled assemblies.

A typical portable means 30 is of a convenient size to wear (about 4×4×1.5 inches). The portable means 30 will typically be placed at the level of the public symphysis and maintained there with the help of a waist belt. The portable means will continuously record (in a solid state memory, on a cassette tape, or the like), in one form or another (in raw or compressed data format), the data reported thereto by the first and second transducer means 16, 20, so that the data can be subsequently transferred to a host computer for processing and plotting. Accordingly, the portable means 30 typically will include a battery, amplifiers, analogue-to-digital converters (for digitizing the pressure signals), a solid state memory or tape recorder, and the like. The portable means 30 may be a cassette sub-unit, such as a modification of the Gaeltec GP III or Oxford Med System 4-24. In order to maintain the portable means as small and compact as possible, typically the data will simply be recorded therein in a solid state memory, and then reproduced in graphical strip form (as a function of time) periodically by an external device (such as a host computer) which also determines and exhibits the difference in graphical strip form. Thus, after completion of each study, the portable means 30 will be operatively connected to a computer or playback unit (not shown), such as the DB-2 Replay Oxford Medical System unit, which will transpose the recorded signals from the portable means 30 to a strip-chart recorder (not shown) such as the Model 2100-Euro System (available from Disa Electronics), which uses a microprocessor and continuously graphically displays up to a 24 hour accumulation of abdominal and urethral pressure signals as well as the difference therebetween.

Figure 2:
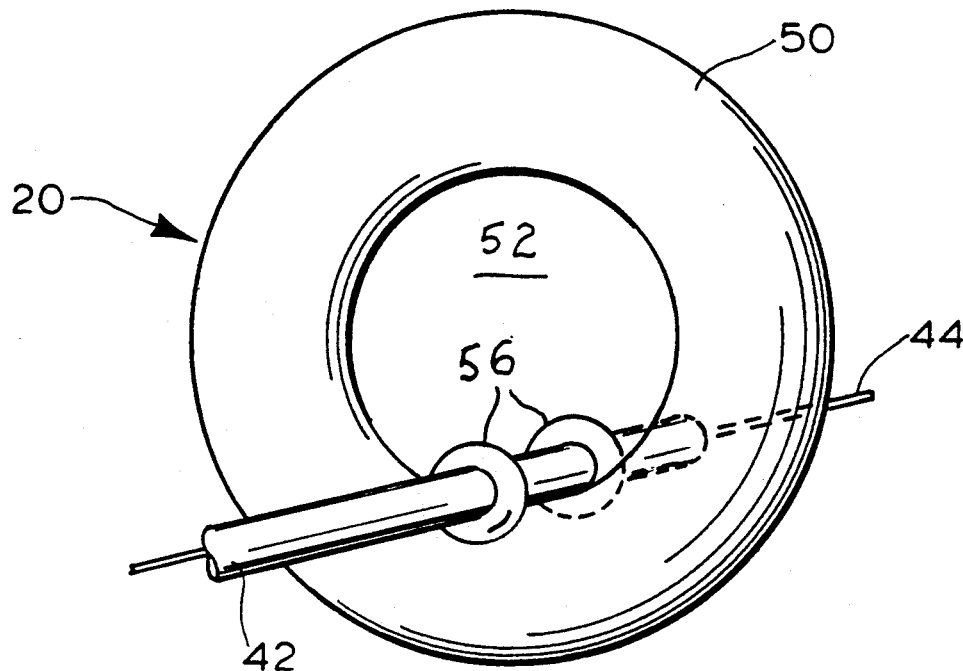
FIG. 2 is an isometric view, to a greatly enlarged scale, of the transvaginal monitor thereof.

Referring now to FIG. 2 as well, the second transducer means 20 is similar to the first transducer means 16 and includes a catheter 42 and a pressure-sensitive microtip transducer 44 mounted at the tip thereof. Via the catheter 42, the microtip transducer 44 is securely mounted on a soft, inflatable vaginal pessary 50. Such vaginal supportive pessaries have long been used in the treatment of varying degrees of uterine prolapse and pelvic floor relaxation, and there are a variety of different types of pessaries from which the most suitable may be selected. A preferred vaginal latex pessary is the Inflato Ball Pessary available from Milex, Inc. Its design permits individualized fitting and adjustment by varying the amount of air pressure within the pessary and, additionally, it is available in a variety of different sizes. Its design permits a transducer to be mounted securely through the existing opening 52 through the center of the pessary 50 in such a way that the pressure sensitive transducer tip 44 is not touching any of the vaginal walls, an essential requirement for accurate measurement.

In order to adapt the inflatable pessary 50 for use in the present invention, a pair of rings 56 are secured to the inner surface of the pessary 50 by gluing, welding, vulcanizing, or other measures not adversely affecting the integrity of the pessary or deleteriously affecting the vagina when the apparatus is in place. The rings 56 are preferably formed of silicone or like inert elastomeric materials suitable for use within the body. A tube or catheter 42 is then secured through and to the inner surface of both rings 56 by glue, adhesive, vulcanizing or welding, much as the rings 56 are secured to the pessary 50. Like the rings 56, the catheter 42 is preferably formed of silicone or similar inert elastomeric material. The rings 56 typically have an inner diameter of 3-4 millimeters, and the catheter 42 typically has an inner diameter of about 2-3 millimeters.

Figure 3:
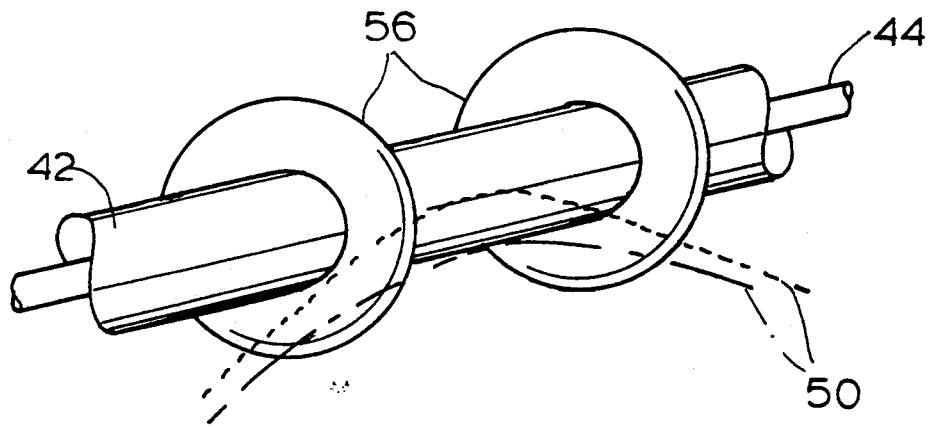
FIG. 3 is an enlarged fragmentary isometric view of a portion of FIG. 2.

The microtip transducer 44 is then slid through the catheter 42 so that it projects from the distal end thereof. The microtip transducer 44 typically has an outside diameter of about 2 millimeters so that it is snugly but releasably held by the catheter 42, and therefore secured to the rings 56 and the pessary 50. Since the microtip transducer 44 is very expensive relative to the pessary 50, rings 56 and catheter 42, the transducer 44 is preferably releasable from the catheter 42 so that it may be reused. The fixation of the microtip transducer 44 within the catheter 42 is determined in the first instance by the snugness of the fit between the outer diameter of the transducer and the inner diameter of the catheter, the snugness enabling the transducer to be inserted with the pessary as a unit into the patient's vagina 22. Referring now to FIG. 3, once the unit is inserted into the patient's vagina 22, the inflation of the pessary 50 from the deflated configuration (indicated in phantom line) to the inflated configuration (indicated in solid line) partially collapses the catheter and thus even more securely fixes the microtip transducer 44 to the catheter 42 so that no accidental separation will occur even during ambulatory motion of the patient 14. On the other hand, once the inflatable pessary 50 has been deflated (i.e., returned to the phantom line configuration) and removed from the patient, the catheter 42 resumes its original configuration and thereby permits easy withdrawal of the microtip transducer 44 therefrom.

Optimally, the pessary 50 maintains itself (and the microtip transducer 44) in the upper two thirds of the vagina 22, above the urogenital diaphragm, where the transvaginal pressure measurements have been shown in non ambulatory studies not only to reflect intraabdominal pressure more accurately than transrectal measurements, but also apparently to give a detrusor trace which is more reflective of actual detrusor activity. The pessary not only comfortably fits above the urogenital diaphragm, but also allows for egress of uterovaginal discharge.

While the second or vaginal transducer means 20 has been described hereinabove in terms of a preferred embodiment employing a modified form of a commercially available inflatable pessary, clearly a variety of similar devices may be used for the same function. In particular, if the inflatable pessary is especially constructed to releasably receive and retain the catheter containing the microtip transducer, a more direct connection between the microtip transducer, catheter and the pessary may be used which still insures that the microtip transducer remains spaced from the vaginal walls so that such walls do not interfere with its pressure readings.

While the second transducer means 20 may utilize a resilient pessary as a floor to support the transducer (as opposed to an inflatable pessary), an inflatable pessary is preferred as it permits a better fitting of the pessary within the vagina. Further, the inflatable pessary, when inflated, precludes unintended separation of the transducer therefrom, but, when deflated, enables easy separation of the transducer therefrom—a feature not obtainable with a resilient pessary.

While the transvaginal and bladder pressure traces will demonstrate much greater activity during ambulation, they nevertheless subtract well to give a stable detrusor pressure trace. Although the bladder and transvaginal activity before subtraction is due to genuine intraabdominal pressure changes, this can be deemed "noise artifact" in terms of the measurements that are of interest according to the present invention.

Whether laboratory, overnight or 24-hour bladder monitoring is performed, the patient will keep a diary of the following: strong urge to void, urge to void accompanied or unaccompanied by a void, change of position, type of activity during leaking, voiding events (voluntary or involuntary, including leaks), drinking events and sleep, as well as the volume of liquid consumed.

At least initially, infection, malignancy and pregnancy should be ruled out in all patients prior to use of the apparatus. In the absence of the above named conditions, and in light of the fact that bladder catheters are routinely used therapeutically for bladder drainage and for diagnostic studies, and that vaginal supportive pessaries have been used therapeutically for hundreds of years, the apparatus is deemed a relatively safe diagnostic (and potentially therapeutic) tool.

It will be appreciated by those skilled in the art that the commercially available first or bladder transducer means 16 typically includes not only a pressure sensitive microtip transducer 34 adapted to be received in the bladder 12, but also a pressure sensitive microtip transducer (not shown) which is disposed lower, in the urethra, for sensing and measuring urethral pressure. Similarly, the commercially available portable means 30 typically includes not only means for recording the bladder pressure (as measured by the first transducer means 16) and an abdominal pressure (typically measured by a transrectal transducer means, but here by a transvaginal transducer means 20), but also means (not shown) for recording the urethral pressure. For expository purposes, these commercially available units have been described only in terms of their pertinent functions for the present invention, so that the additional urethral transducer and recorder aspects have not been discussed hereinabove. For the purpose of the present invention, the main function of the optional urethral transducer would be to assure proper positioning of the bladder transducer means 16 within the bladder 12.

The present invention permits accurate and acceptable means of continuous bladder monitoring with improved diagnostic capabilities, especially in patients with sensory urgency as a sole symptom. It has been found that ambulatory monitoring reveals occult detrusor or bladder contractions in patients who have, apparent urgency, yet test normally in conventional laboratory (static) urodynamic testing. The present invention allows these patients to be diagnosed and therefore receive accurate treatment.

The patient may move freely in her own home and own environment for the duration of the testing, including overnight studies. The present invention also finds utility i various treatment protocols which utilize biofeedback, electrical stimulation or pharmacological agents, enabling the patients to be monitored on an ambulatory basis. The invention may also be useful in allowing investigation into biofeedback devices designed to help the patient practice contractive exercises as a means of achieving continence.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. A vesicovaginal apparatus for ambulatory monitoring of the detrusor pressure exerted by a bladder comprising:
   (A) first transducer means configured and dimensioned for insertion into and retention by the bladder of a wearer during ambulatory motion for sensing the total pressure within the bladder;
   (B) second transducer means configured and dimensioned for insertion into and retention by the vagina of a wearer during ambulatory motion for sensing the pressure within the vagina, said second transducer means comprising an inflatable and deflatable pessary and a transducer for sensing pressure mounted thereon, said pessary when inflated precluding unintended separation of said transducer therefrom but when deflated enabling easy separation of said transducer therefrom; and
   (C) portable means in operative communication with said first and second transducer means for recording the total pressure sensed in the bladder and the pressure sensed in the vagina, with the difference indicating the detrusor pressure exerted by the bladder of the wearer.

2. The apparatus of claim 1 wherein said second transducer means is configured and dimensioned for insertion into and retention by the upper two-thirds of the vagina.

3. The apparatus of claim 1 wherein each of said first and second transducer means includes a microtip transducer for sensing pressure.

4. The apparatus of claim 3 wherein said transducers of said first and second transducer means are disposed in the bladder and the vagina, respectively.

5. The apparatus of claim 3 wherein said portable disposed externally of the body of the wearer.

6. A vesicovaginal apparatus for ambulatory monitoring of the detrusor pressure exerted by a bladder comprising:
   (A) first transducer means configured and dimensioned for insertion into and retention by the bladder of a wearer during ambulatory motion for sensing the total pressure within the bladder;
   (B) second transducer means configured and dimensioned for insertion into and retention by the upper two-thirds of the vagina of a wearer during ambulatory motion for sensing the pressure within the vagina, said second transducer means comprising an inflatable pessary and a transducer for sensing pressure, releasably mounted thereon said inflatable pessary when inflated precluding unintended separation of said transducer therefrom but when deflated enabling easy separation of said transducer therefrom; and
   (C) portable means disposed externally of the body of the wearer and in operative communication with said first and second transducer means for recording the total pressure sensed in the bladder and the pressure sensed in the vagina, with the difference indicating the detrusor pressure exerted by the bladder of the wearer.

* * * * *